United States Patent
Chen et al.

(10) Patent No.: US 11,913,083 B2
(45) Date of Patent: Feb. 27, 2024

(54) ASSAY FOR DETECTING CLOSELY-RELATED SEROTYPES OF HUMAN PAPILLOMAVIRUS (HPV)

(71) Applicant: BECTON DICKINSON AND COMPANY, Franklin Lakes, NJ (US)

(72) Inventors: Chi Chen, Cockeysville, MD (US); Hugh J. Peck, Jarrettsville, MD (US); Michael Porter, Baltimore, MD (US); Gregory A. Richart, York, PA (US); Ray A. McMillian, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 530 days.

(21) Appl. No.: 17/094,908

(22) Filed: Nov. 11, 2020

(65) Prior Publication Data
US 2021/0071272 A1 Mar. 11, 2021

Related U.S. Application Data

(62) Division of application No. 15/843,957, filed on Dec. 15, 2017, now Pat. No. 10,865,455, which is a division of application No. 14/179,113, filed on Feb. 12, 2014, now Pat. No. 9,868,997, which is a division of application No. 13/028,589, filed on Feb. 16, 2011, now Pat. No. 8,658,397.

(60) Provisional application No. 61/304,941, filed on Feb. 16, 2010.

(51) Int. Cl.
C12Q 1/70 (2006.01)

(52) U.S. Cl.
CPC ..................... C12Q 1/708 (2013.01)

(58) Field of Classification Search
CPC ...... C12Q 1/708; C12Q 1/6876; C12Q 1/686; C12Q 1/68
See application file for complete search history.

(56) References Cited

U.S. PATENT DOCUMENTS

| | | |
|---|---|---|
| 5,538,848 A | 7/1996 | Livak et al. |
| 5,691,134 A | 11/1997 | Kilpatrick et al. |
| 5,698,394 A | 12/1997 | Duhamel et al. |
| 5,705,627 A | 1/1998 | Manos et al. |
| 6,143,494 A | 11/2000 | Kilpatrick |
| 6,214,555 B1 | 4/2001 | Leushner et al. |
| 7,183,053 B2 | 2/2007 | Gocke et al. |
| 2002/0061516 A1 | 5/2002 | Vidaud et al. |
| 2006/0257894 A1 | 11/2006 | Doumith et al. |
| 2009/0215030 A1 | 8/2009 | Jeney |

FOREIGN PATENT DOCUMENTS

| | | |
|---|---|---|
| EP | 0624643 A2 | 11/1994 |
| EP | 1997914 A1 | 12/2008 |
| WO | 03019143 A2 | 3/2003 |
| WO | 2004030636 | 4/2004 |
| WO | 2004031416 A1 | 4/2004 |
| WO | 2007057669 A2 | 5/2007 |
| WO | 2009057993 A1 | 5/2009 |

OTHER PUBLICATIONS

Harwood et al., Journal of Clinical Microbiology, vol. 37, No. 11, pp. 1545-1555, Nov. 1999.*
Notice of Allowance dated Mar. 28, 2023 in Brazilian Patent Application No. 112012020470-0.
Extended European Search Report for Application No. EP11745156 dated Jun. 25, 2013.
International Search Report Application No. PCT/US2011/025046, dated Nov. 18, 2011.
Broccolo, et al., "Automated extraction and quantitation of oncogenic HPV genotypes from cervical samples by a real-time PCR-based system", Journal of Virological Methods, Elsevier BV, NL, vol. 148, No. 1-2, Nov. 28, 2007, XP022487592, (Nov. 28, 2007), pp. 48-57.
Chen, T. C., et al., J. Clin Microbial., 44(6), (2006), pp. 2212-2219.
Clavel, et al., British J. Cancer 80(9), (1999), pp. 1306-1311.
Gravitt, et al., Journal of Clinical Microbiology 38(1), (2000), pp. 357-361.
Han, et al., ""Simultaneous amplification and identification of 25 human papillomavirus types with Templex technology"", Journal of Clinical Microbiology, American Society for Microbiology, Washington, DC, US, [Online] vol. 44, No. 11, Nov. 1, 2006, XP002675146, (Nov. 1, 2006), pp. 4157-4162.
Harwood, et al., Journal of Clinicical Microbiology, 37(11), (1999), pp. 3545-3555.
Holland, et al., Proc. Natl. Acad. Sci. USA 88, (1991), pp. 7276-7280.
Iftner, et al., Journal of Clinical Microbiology, vol. 47, No. 7, (Jul. 2009), pp. 2106-2113.
Josefsson, et al., Journal of Clinical Microbiology, 37(3), (1999), pp. 490-496.
Kleter, et al., Journal of Clinical Microbiology 37(8), (1999), pp. 2508-2517.

(Continued)

*Primary Examiner* — Cynthia B Wilder
(74) *Attorney, Agent, or Firm* — Sheppard, Mullin, Richter & Hampton LLP

(57) ABSTRACT

A real time Taq-Man PCR assay for detecting multiple serotypes of human papillomavirus (HPV) wherein the number of serotypes detected exceeds the number of colorimetric channels for detection. A biological sample is combined with three oligonucleotide primer/probe sets such that the probes and primers anneal to a target sequence. Each primer/probe set is at least preferential for a specific serotype of an organism. The first and second primer/probe sets are degenerate with respect to each other. The third primer/probe set is not degenerate with respect to the first and second primer/probe sets and discriminates for a third serotype. The third primer/probe set has a signal moiety that emits signal at a wavelength that is the same or different from the wavelength emitted by the signal moiety of the degenerate primer/probe set probes. The target sequences, if present, are amplified and detected.

19 Claims, 4 Drawing Sheets

Specification includes a Sequence Listing.

(56) References Cited

OTHER PUBLICATIONS

Lin, B., et al., Use of oligonucleotide microarrays for rapid detection and serotyping of acute respiratory disease-associated adenoviruses J. Clin Microbial., vol. 42, No. 7, (Jul. 2004), pp. 3232-3239.

McMurray, et al., Int. J. Exp, Pathol. 82(1), (2001), pp. 15-31.

Moberg, Martin, et al., "Real-time PCR-based system for simultaneous quantification of human papillomavirus types associated with high risk of cervical cancer", Journal of Clinical Microbiology, American Society for Microbiology, Washington, DC, US, vol. 41, No. 7, Jul. 1, 2003, (Jul. 1, 2003), pp. 3221-3228.

Nanda, et al., Journal of Virological Methods, 152;, (2008), pp. 18-24.

Nishiwaki, Morie, et al., "Genotyping of human papillomaviruses by a novel one-step typing method with multiplex PCR and clinical applications", Journal of Clinical Microbiology, American Society for Microbiology, Washington, DC, US, vol. 46, No. 4, Apr. 1, 2008, (Apr. 1, 2008), pp. 1161-1168.

Preparata, et al., Journal of Computational Biology, 11(4), (2004), pp. 753-765.

Rose, et al., Nucleic Acids Research, 26(7), (1998), pp. 1628-1635.

Schmitz, M., et al., "Quantitative multiplex PCR assay for the detection of the seven clinically most relevant high-risk HPV types", Journal of Clinical Virology, Elsevier, Amsterdam, NL, vol. 44, No. 4, Apr. 1, 2009, XP026072919, (Apr. 1, 2009), pp. 302-307.

Swan, et al., Journal of Clinical Microbiology 35(4), (1997), pp. 886-891.

Swan, et al., "Human papillomavirus (HPV) DNA copy number is dependent on grade of cervical disease and HPV type", Journal of Clinical Microbiology, American Society for Microbiology, Washington, DC, US, vol. 37, No. 4, Apr. 1, 1999, XP002251200, (Apr. 1, 1999), pp. 1030-1034.

Tucker, et al., Molecular Diagnosis, 6(1);, (2001), pp. 38-47.

Walker, et al., "Strand displacement amplification—an isothermal, in vitro DNA amplification technique", Nucleic Acids Researc, vol. 20, No. 7,, (1992), pp. 1691-1696.

Ylitalo, Nathalie, Journal of Clinical Microbiology, vol. 33, No. 7, (1995), pp. 1822-1828.

\* cited by examiner

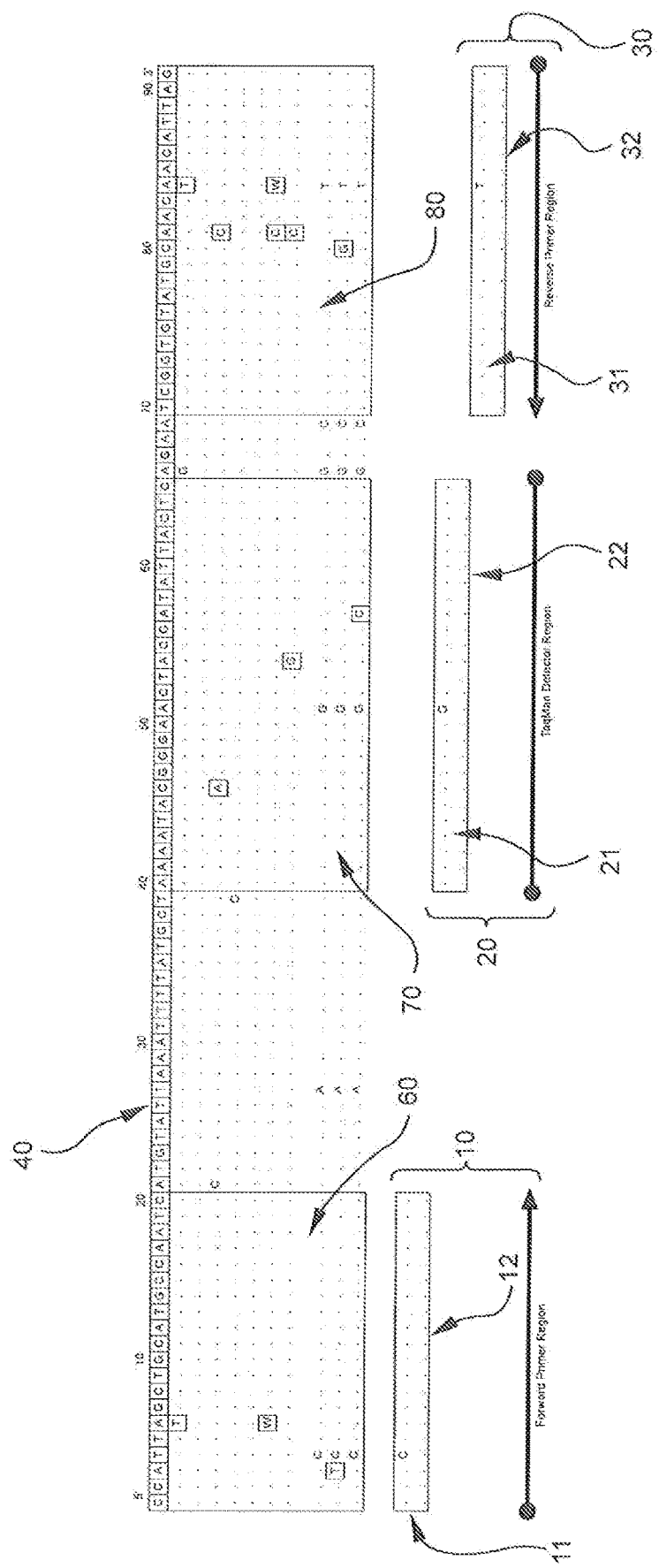
FIG. 1 qPCR Degenerate Primer/Probe Set for Detecting HPV Types 39 & 68; E6-gene DNA

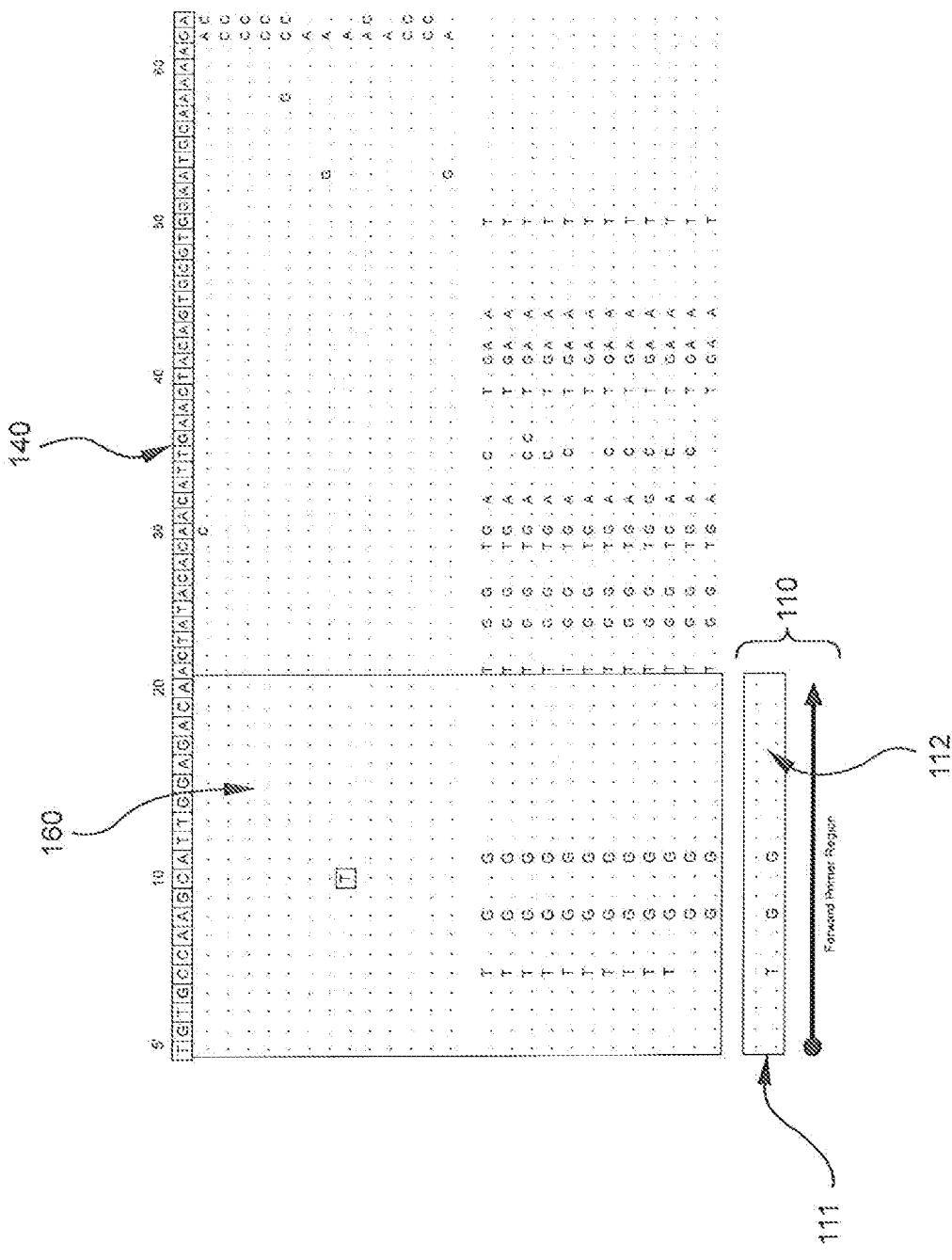
FIG. 2A qPCR Degenerate Primer/Probe Design for Detecting of HPV Types 33 & 58; E6-gene DNA

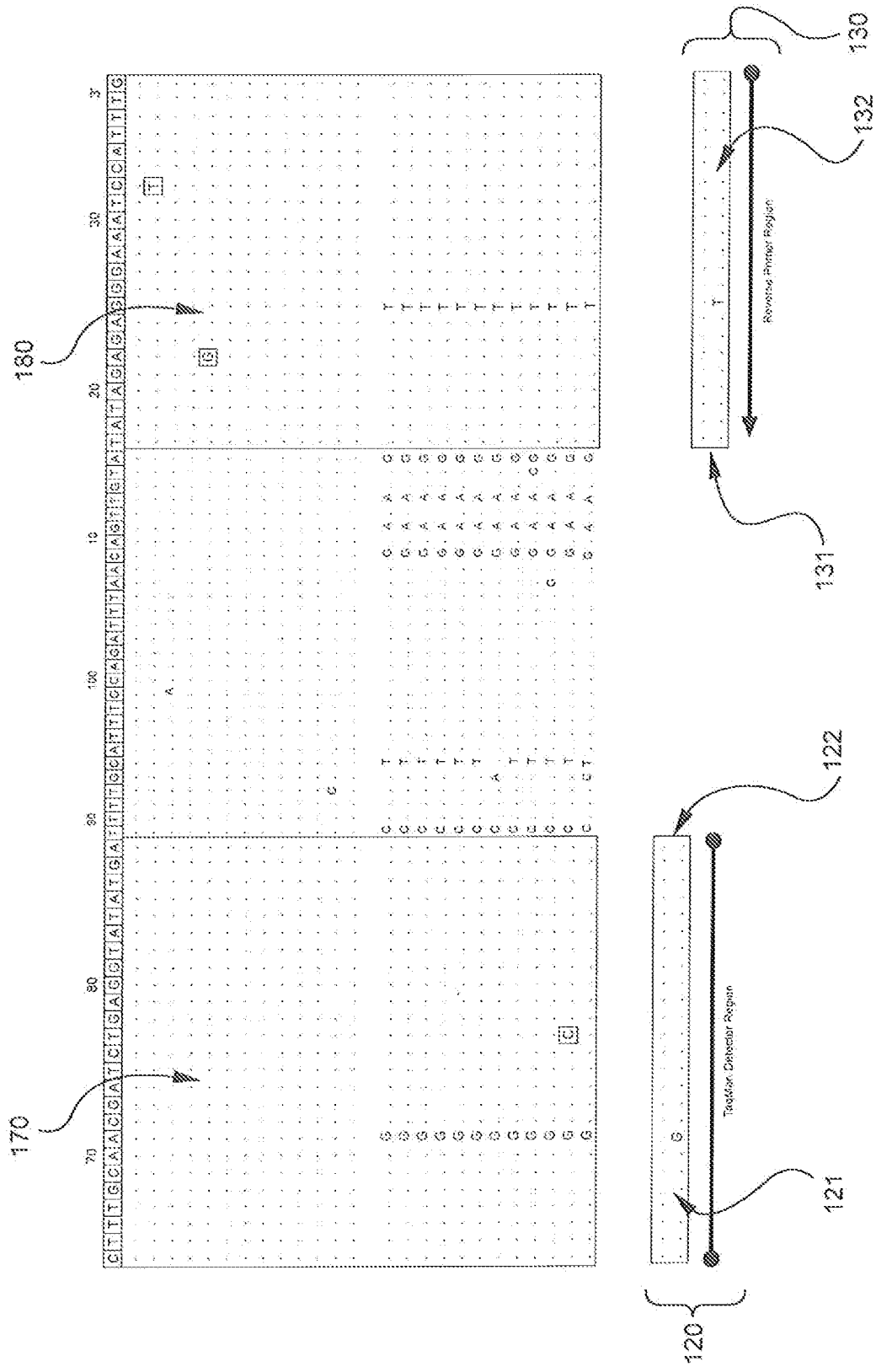
FIG. 2B qPCR Degenerate Primer/Probe Design for Detecting of HPV Types 33 & 58; E6-gene DNA

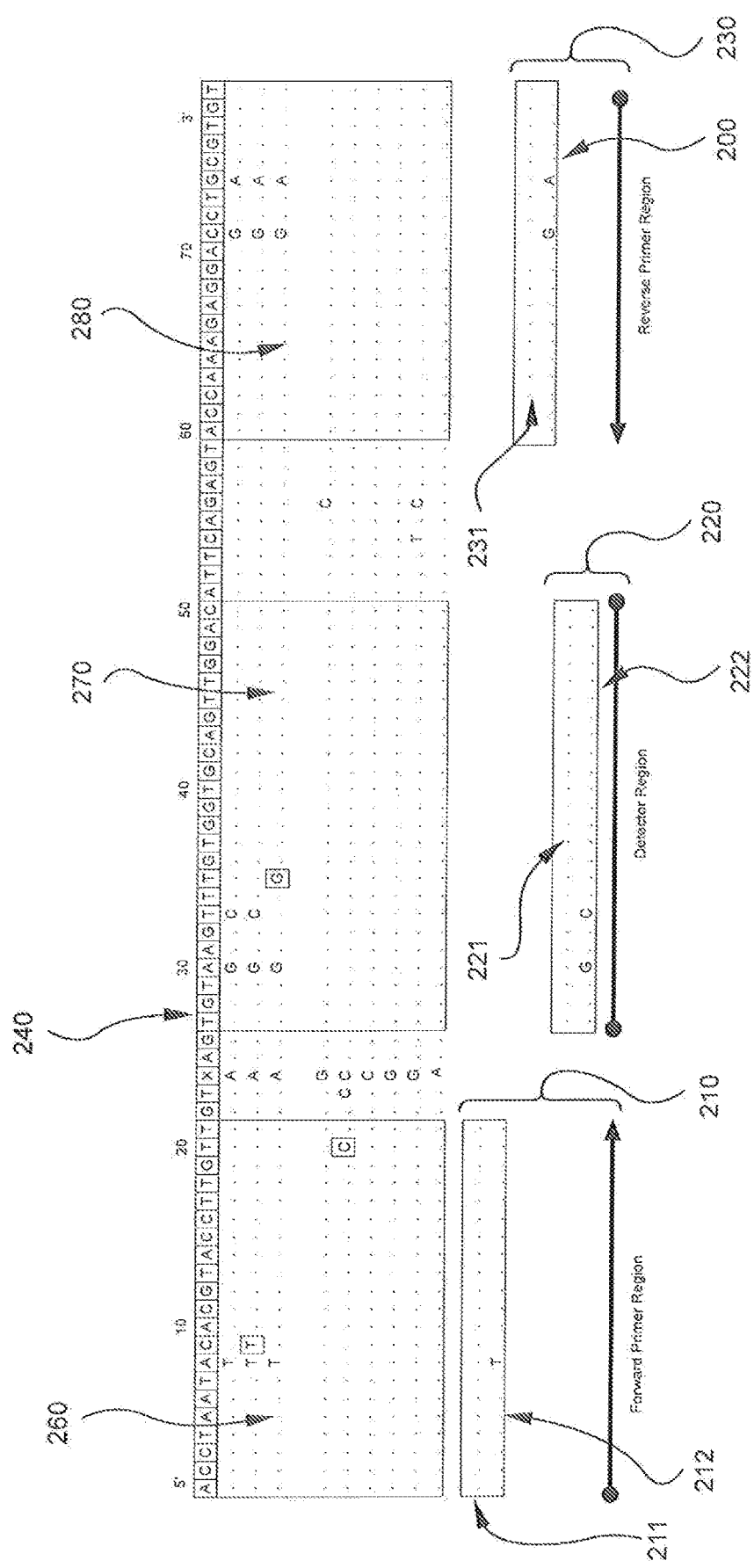
FIG. 3 qPCR Degenerate Primer/Probe Set for Detecting of HPV Types 56 & 66; E7-gene DNA

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
ccactagctg catgccaatc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
ccattagctg catgccaatc                                                    20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ctaatgtagt tgcatacacc ga                                                 22

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
ctaatgttgt tgcatacacc ga                                                 22

<210> SEQ ID NO 5
<211> LENGTH: 26
<212> TYPE: DNA
<213> ORGANISM: Artificial Sequence
<220> FEATURE:
<223> OTHER INFORMATION: Synthetic Probe

<400> SEQUENCE: 5
gagtaatatc gtagctcccg tatttt                                             26

<210> SEQ ID NO 6
<211> LENGTH: 26
<212> TYPE: DNA
<213> ORGANISM: Artificial Sequence
<220> FEATURE:
<223> OTHER INFORMATION: Synthetic Probe

<400> SEQUENCE: 6
gagtaatatc gtagttcccg tatttt                                             26

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 7
tgtgccaagc attggagaca                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
tgtgtcaggc gttggagaca                                                    20

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
caaatggatt tccctctcta ta                                                 22

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
caaatggatt tccatctcta ta                                                 22

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
cctctctata tacaactgtt aaa                                                23

<210> SEQ ID NO 12
<211> LENGTH: 24
<212> TYPE: DNA
<213> ORGANISM: Artificial Sequence
<220> FEATURE:
<223> OTHER INFORMATION: Synthetic Primer

<400> SEQUENCE: 12
ccatctctat acactattct taaa                                               24

<210> SEQ ID NO 13
<211> LENGTH: 24
<212> TYPE: DNA
<213> ORGANISM: Artificial Sequence
<220> FEATURE:
<223> OTHER INFORMATION: Synthetic Primer

<400> SEQUENCE: 13
aaatggattt ccctctctat atac                                               24
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic Primer

<400> SEQUENCE: 14
aaatggattt ccatctctat acac                                              24

<210> SEQ ID NO 15
<211> LENGTH: 25
<212> TYPE: DNA
<213> ORGANISM: Artificial Sequence
<220> FEATURE:
<223> OTHER INFORMATION: Synthetic Probe

<400> SEQUENCE: 15
tcatatacct cagatcgttg caaag                                             25

<210> SEQ ID NO 16
<211> LENGTH: 25
<212> TYPE: DNA
<213> ORGANISM: Artificial Sequence
<220> FEATURE:
<223> OTHER INFORMATION: Synthetic Probe

<400> SEQUENCE: 16
tcatatacct cagatcgctg caaag                                             25

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
acctaataca cgtaccttgt t                                                 21

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
acctaattca cgtaccttgt t                                                 21

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
acacgcaggt cctctttggt                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 20
acacgtagct cctctttggt                                           20

<210> SEQ ID NO 21
<211> LENGTH: 25
<212> TYPE: DNA
<213> ORGANISM: Artificial Sequence
<220> FEATURE:
<223> OTHER INFORMATION: Synthetic Probe

<400> SEQUENCE: 21
tgtaagtttg tggtgcagtt ggaca                                     25

<210> SEQ ID NO 22
<211> LENGTH: 25
<212> TYPE: DNA
<213> ORGANISM: Artificial Sequence
<220> FEATURE:
<223> OTHER INFORMATION: Synthetic Probe

<400> SEQUENCE: 22
tgtgagcttg tggtgcagtt ggaca                                     25

<210> SEQ ID NO 23
<211> LENGTH: 25
<212> TYPE: DNA
<213> ORGANISM: Artificial Sequence
<220> FEATURE:
<223> OTHER INFORMATION: Synthetic Probe

<400> SEQUENCE: 23
tgtgagttgg tggtgcagtt ggaca                                     25

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
gcagtatgca aacaatgttc ac                                        22

<210> SEQ ID NO 25
<211> LENGTH: 23
<212> TYPE: DNA
<213> ORGANISM: Artificial Sequence
<220> FEATURE:
<223> OTHER INFORMATION: Synthetic Primer

<400> SEQUENCE: 25
tagtaattgc ctctaatgta gta                                       23

<210> SEQ ID NO 26
<211> LENGTH: 25
<212> TYPE: DNA
<213> ORGANISM: Artificial Sequence
<220> FEATURE:
<223> OTHER INFORMATION: Synthetic Probe

<400> SEQUENCE: 26
cctgctataa cgtctatact ctcta                                     25
```

```
<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
ctcagaggag gaggatgaag                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
tgaacacctg caacacggag                                                20

<210> SEQ ID NO 29
<211> LENGTH: 22
<212> TYPE: DNA
<213> ORGANISM: Artificial Sequence
<220> FEATURE:
<223> OTHER INFORMATION: Synthetic Probe

<400> SEQUENCE: 29
ctaccagaaa gacgggctgg ac                                             22

<210> SEQ ID NO 30
<211> LENGTH: 21
<212> TYPE: DNA
<213> ORGANISM: Artificial Sequence
<220> FEATURE:
<223> OTHER INFORMATION: Synthetic Primer

<400> SEQUENCE: 30
ggagaaacat tagaggctga a                                              21

<210> SEQ ID NO 31
<211> LENGTH: 23
<212> TYPE: DNA
<213> ORGANISM: Artificial Sequence
<220> FEATURE:
<223> OTHER INFORMATION: Synthetic Primer

<400> SEQUENCE: 31
atagaggttt taggcatcta taa                                            23

<210> SEQ ID NO 32
<211> LENGTH: 24
<212> TYPE: DNA
<213> ORGANISM: Artificial Sequence
<220> FEATURE:
<223> OTHER INFORMATION: Synthetic Probe

<400> SEQUENCE: 32
accgttacat gagctgctga tacg                                           24

<210> SEQ ID NO 33
<211> LENGTH: 21
<212> TYPE: DNA
<213> ORGANISM: Artificial Sequence
<220> FEATURE:
<223> OTHER INFORMATION: Synthetic Primer
```

-continued

```
<400> SEQUENCE: 33
gaagttgacc ttgtgtgcta c                                              21

<210> SEQ ID NO 34
<211> LENGTH: 23
<212> TYPE: DNA
<213> ORGANISM: Artificial Sequence
<220> FEATURE:
<223> OTHER INFORMATION: Synthetic Primer

<400> SEQUENCE: 34
attaactcca tctggttcat ctt                                            23

<210> SEQ ID NO 35
<211> LENGTH: 24
<212> TYPE: DNA
<213> ORGANISM: Artificial Sequence
<220> FEATURE:
<223> OTHER INFORMATION: Synthetic Probe

<400> SEQUENCE: 35
attacctgac tccgactccg agaa                                           24

<210> SEQ ID NO 36
<211> LENGTH: 91
<212> TYPE: DNA
<213> ORGANISM: Human papillomavirus types 39 & 68

<400> SEQUENCE: 36
ccattagctg catgccaatc atgtattaaa ttttatgcta aaatacggga actacgatat    60
tactcagaat cggtgtatgc aacaacatta g                                   91

<210> SEQ ID NO 37
<211> LENGTH: 138
<212> TYPE: DNA
<213> ORGANISM: Human papillomavirus types 33 & 58

<400> SEQUENCE: 37
tgtgccaagc attggagaca actatacaca acattgaact acagtgcgtg gaatgcaaaa   60
agactttgca acgatctgag gtatatgatt ttgcatttgc agatttaaca gttgtatata  120
gagagggaaa tccatttg                                                 138

<210> SEQ ID NO 38
<211> LENGTH: 79
<212> TYPE: DNA
<213> ORGANISM: Human papillomavirus types 56 & 66

<400> SEQUENCE: 38
acctaataca cgtaccttgt tgtragtgta agtttgtggt gcagttggac attcagagta    60
ccaaagagga cctgcgtgt                                                 79
```

ASSAY FOR DETECTING CLOSELY-RELATED SEROTYPES OF HUMAN PAPILLOMAVIRUS (HPV)

This application is a divisional application of U.S. patent application Ser. No. 15/843,957, which was filed on Dec. 15, 2017, allowed, which application is a divisional application of U.S. patent application Ser. No. 14/179,113, which was filed on Feb. 14, 2014, issued as U.S. Pat. No. 9,868,997 on Jan. 16, 2018, which application is a divisional application of U.S. patent application Ser. No. 13/028,589, which was filed on Feb. 16, 2011, issued as U.S. Pat. No. 8,658,397 on Feb. 25, 2014, and claims the benefit of the filing date of U.S. Provisional Patent Application No. 61/304,941 filed on Feb. 16, 2010, the disclosures of which are hereby incorporated herein by reference.

SEQUENCE LISTING

The instant application contains a Sequence Listing which was submitted via EFS-Web in prior patent application Ser. No. 13/028,599, which was filed on Feb. 16, 2011 and issued as U.S. Pat. No. 8,658,397 on Feb. 25, 2014 and Ser. No. 14/179,113 which was filed on Feb. 12, 2014 and issued as U.S. Pat. No. 9,868,997, and Ser. No. 15/843,957, which was filed on Dec. 15, 2017, allowed, and in this application and is hereby incorporated by reference in its entirety. Said ASCII copy, created on Jan. 31, 2011 is named Sequence Listing for Detecting Related Serotypes of HPV, and is 7.55 kilobytes in size.

BACKGROUND OF THE INVENTION

More than 80 types of human papillomaviruses (HPVs) have been identified. The different types of HPV cause a wide variety of biological phenotypes, from benign proliferative warts to malignant carcinomas (for review, see McMurray et al., Int. J. Exp, Pathol. 82(1): 15-33 (2001)). HPV6 and HPV11 are the types most commonly associated with benign warts, whereas HPV16 and HPV18 are the high-risk types most frequently associated with malignant lesions. Determination of the specific type of HPV in a clinical sample is, therefore, critical for predicting risk of developing HPV-associated disease.

Several nucleic acid-based methods have been utilized to identify and quantify specific HPV types in clinical samples, such as detection of viral nucleic acid by in situ hybridization, Southern blot analysis, hybrid capture or polymerase chain reaction (PCR). The Hybrid Capture® II (Qiagen, Inc., Valencia, CA) assay utilizes antibody capture and non-radioactive signal detection, but detects only a single target of a given set of HPV types (See, e.g., Clavel et al., British J. Cancer 80(9): 1306-11 (1999)). Additionally, because the Hybrid Capture® II assay uses a cocktail of RNA probes (probe cocktails are available for high risk or low-risk HPV types), it does not provide information as to the specific HPV type detected in a sample, but rather provides only a positive or negative for the presence of high-risk or low-risk HPV. Similarly, many PCR-based methods often involve amplification of a single specific HPV target sequence followed by blotting the resulting amplicon to a membrane and probing with a radioactively labeled oligonucleotide probe.

Other methods exploit the high homology between specific HPV genes of different types through the use of commercially available consensus primers capable of PCR amplification of numerous HPV types present in a sample. The presence of a specific HPV type is then identified using a type-specific oligonucleotide probe. See, e.g., Kleter et al., Journal of Clinical Microbiology 37(8): 2508-2517 (1999); Gravitt et al., Journal of Clinical Microbiology 38(1): 357-361 (2000). Similarly, assays that utilize degenerate PCR primers take advantage of the homology between HPV types, allowing detection of a greater number of HPV types than methods utilizing specific primer sets. See, e.g. Harwood et al., Journal of Clinical Microbiology 37(11): 3545-3555 (1999). Such assays also require additional experimentation to identify specific HPV types.

The PCR methods described above can be associated with several problems. For example, differences in reaction efficiencies among HPV types can result in disproportionate amplification of some types relative to others. Additionally, the equilibrium for amplification will be driven towards those types that exist at higher copy numbers in a sample, which will consume the PCR reaction components, thus making amplification of the minor HPV types less likely.

Also described in the art is a 5' exonuclease fluorogenic PCR-based assay (Taq-Man PCR) which allows detection of PCR products in real-time and eliminates the need for radioactivity. See, e.g., U.S. Pat. No. 5,538,848; Holland et al, Proc. Natl. Acad. Sci. USA 88: 7276-7280 (1991). This method utilizes a labeled probe, comprising a fluorescent reporter (fluorophore) and a quencher that hybridizes to the target DNA between the PCR primers. Excitation of the fluorophore results in the release of a fluorescent signal by the fluorophore which is quenched by the quencher. Amplicons can be detected by the 5'-3' exonuclease activity of the TAQ DNA polymerase, which degrades double-stranded DNA encountered during extension of the PCR primer, thus releasing the fluorophore from the probe. Thereafter, the fluorescent signal is no longer quenched and accumulation of the fluorescent signal, which is directly correlated with the amount of target DNA, can be detected in real-time with an automated fluorometer.

Taq-Man PCR assays have been adapted for HPV type detection. Swan et al. (Journal of Clinical Microbiology 35(4): 886-891 (1997)) disclose a fluorogenic probe assay that utilizes type-specific HPV primers that amplify a portion of the L1 gene in conjunction with type-specific probes. The Swan et al. assay measures fluorescent signal at the end of a fixed number of PCR cycles (endpoint reading) and not in real-time.

Josefsson et al. (Journal of Clinical Microbiology 37(3): 490-96 (1999)) report a Taq-Man assay that targets a highly conserved portion of the E1 gene in conjunction with type-specific probes labeled with different fluorescent dyes. A number of HPV types were amplified by utilizing a mixture of specific and degenerate primers. Josefsson et al. utilized up to three type-specific probes per assay, which were designed to detect a portion of the E1 gene from different HPV types. Unlike the Swan et al. assay, Josefsson et al. measured the accumulation of fluorescence in real-time.

Tucker et al. (Molecular Diagnosis 6(1): 39-47 (2001)) describe an assay that targets a conserved region spanning the E6/E7 junction. Like the Josefsson assay, Tucker et al. employed real-time detection and type-specific fluorescent probes. Tucker et al. also utilized multiplex PCR to simultaneously detect HPV target sequences and either the actin or globin cellular loci in the same reaction tube.

One of the particular challenges with HPV detection is the fact that there are many HPV types of clinical interest. Although multiplex assays for HPV detection are known, the multiplex assays are limited by the number of colorimetric channels for detection. These channels are various wavelengths of light (or ranges or bands of wavelengths). Each channel detects a signal emitted by a signal moiety that emits light at a specific channel wavelength. The number of HPV types that are detected is therefore limited by the number of different, distinctly detectable signal moieties in the assay.

Despite the development of the HPV assays described above, it would be advantageous to develop a multiplex assay that is highly sensitive and reproducible, and that requires reduced man-hours compared to methods disclosed in the art. Given the many HPV types, it would be useful to detect more HPV types than there are detection channels of the assay.

SUMMARY OF THE INVENTION

The present invention is directed to a real-time PCR amplification that deploys Taq-Man chemistry to simultaneously detect more types of HPV than there are channels for detection. In other words, in an assay with N channels, the number of HPV types that are detected is at least N+1.

The assay deploys a primer/probe set for detection of each type of HPV that the assay is configured to detect. Among the various serotypes susceptible for detection by the assay include, for example, HPV types 33, 39, 51, 56, 58, 59, 66 and 68. The skilled person will appreciate that the probe/primer sets described herein might be combined with other primer/probe sets for other types of HPV (e.g. 16, 18, and 45). At least one type is detected using a single primer probe set. In the context of PCR amplification using a Taq-Man assay, the primer probe set is at least a forward primer, a reverse primer and a probe. At least two types are selected by a pair of primer probe sets with oligonucleotide sequences that are degenerate with respect to each other. "Degenerate sequences" as used herein, are two oligonucleotide primers or probes that are complementary to the same locus of the same gene of different closely related types and which have minor sequence variations with respect to each other to make them discriminatory between the two types.

In one embodiment of the present invention, the degenerate primer probes sets are for detection of HPV types 39 and 68. The primer/probe set targets the same locus on the E6 gene of both types. The target length is 91 nucleotides and is illustrated in FIG. 1. The target is only a segment of the entire E6 gene. The target for the degenerate primer/probe set for HPV types 39 and 68 is SEQ ID NO: 36. In a preferred embodiment the signal moieties for both probes is a cyanine dye label commercially available as CY5.

In this embodiment, the primer probe set that is not degenerate discriminates for HPV Type 51. The primer/probe set for type 51 also targets the E6 gene, although in a different locus. In a preferred embodiment the signal moieties for this probe in this primer probe set is FAM, which is specifically identified below.

In a second embodiment of the present invention, the degenerate primer/probes sets are for detection of HPV types 33 and 58. The primer/probe set targets the same locus on the E6 gene of both types. The target length is 138 nucleotides and is illustrated in FIG. 2. The target is only a segment of the entire E6 gene. The target for the degenerate primer/probe set for HPV types 33 and 58 is SEQ ID NO: 37. In a preferred embodiment the signal moieties for both probes is FAM.

In this embodiment, the primer probe set that is not degenerate discriminates for HPV Type 59. The primer/probe set for type 59 also targets the E6 gene, but not necessarily the same locus. In a preferred embodiment the signal moieties for this probe in this primer probe set is CY5, which is specifically identified below.

In a third embodiment of the present invention, the degenerate primer/probes sets are for detection of HPV types 56 and 66. The primer/probe set targets the same locus on the E6 gene of both types. The target length is 79 nucleotides and is illustrated in FIG. 3. The target is only a segment of the entire E6 gene. The target for the HPV type 56 and 66 degenerate primer/probe set is SEQ ID NO: 38. In a preferred embodiment the signal moieties for both probes is CY5.

In this embodiment, the primer probe set that is not degenerate discriminates for HPV Type 59. The primer/probe set for Type 59 targets the E6 gene. In a preferred embodiment the signal moieties for this probe in this primer probe set is CY5, which is specifically identified below. In this embodiment, the same signal moiety that is used for HPV Type 59 is also used for HPV Types 56_66. Since the same dyes are on the same channel, there is no optical discrimination between HPV types 59 and 56 66 in this embodiment.

This embodiment contemplates a multiplex assay that deploys yet another primer/probe set (either degenerate or discriminatory) for yet another HPV serotype (e.g. the degenerate primer/probe set for HPV serotypes 33 and 58). The signal moiety for this other HPV serotype is not CY5, and emits at a wavelength that is detectably different from the emission wavelength of Cy5 (e.g. FAM).

In other embodiments, the signal moiety for the HPV Type 59 probe is FAM, which can be optically distinguished from the CY5 signal moiety for the degenerate primer/probe set for HPV serotypes 56 and 66.

Alternate embodiments contemplate an assay or a probe set or a kit with any and all combinations of the primer/probe sets and the degenerate primer/probe sets described herein. Specifically, any of the primer/probe sets for HPV serotype HPV 51 or HPV 59 can be combined with any of the degenerated primer/probe sets for HPV serotypes HPV 39_68; HPV 33_58; and HPV 56_66. Specifically contemplated is an assay or probe set or a kit which combines the primer/probe set for HPV 51 with the degenerate primer probe set of one or more of HPV 39_68; HPV 33_58; and HPV 56_66. An assay or probe set or a kit which combines the primer/probe set for HPV 59 with the degenerate primer probe set of one or more of HPV 39_68; HPV 33_58; and HPV 56_66. Embodiments where the signal moieties for the probes are the same or different dyes are contemplated. Since a multiplex assay is contemplated, the primer/probe sets can be combined with other primer/probe sets configured to detect the presence or absence of other serotypes of HPV. In those embodiments where the signal moiety for the detector probe in the degenerate primer/probe sets is the same as the signal moiety for the primer/probe set for HPV serotype 51 or 59, it is contemplated that the multiplex assay would include a fourth primer/probe set for a fourth serotype of HPV (e.g. HPV 31, HPV 52, HPV 45, etc.) and that the fourth primer/probe set would have a signal moiety that is different from the signal moieties for the detector probes of the degenerate primer/probe sets and the HPV 51 or 59 primer/probe sets. Also, contemplated herein are multiplex assays in which two degenerate primer/probe sets are combined in one assay. For example, in one microwell, a first degenerate primer/probe set for detecting the present of HPV serotypes 33 and 58 can be combined with a second degenerate primer/probe set for detecting the presence or absence of HPV serotypes 56 and 66. In these embodiments the probes of the first degenerate primer probe set has a signal moiety that emits at wavelength that is detectably different from the emission wavelength of the signal moiety for the second degenerate primer/probe set. In this example the signal moiety for HPV serotypes 33 and 58 probes would be FAM and the signal moiety for HPV serotypes 56 and 66 probes would be CY5.

In addition to the signaling moieties described above, the probes also have a non-fluorescent dark quencher. One example of a suitable dark quencher is BHQ™ 1 (Biosearch Technologies), which is suited for use with the FAM fluorophore. Another example of a suitable quencher is BHQ™ 2 (Biosearch Technologies), which is suited for use with the CY5 fluorophore. Other examples of signaling moieties are well known to those skilled in the art and are not described in detail herein.

As used herein, the term "primer" refers to an oligonucleotide that is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes components which are cofactors, or which affect ionic strength, pH, etc.), and at a suitable temperature. As employed herein, an oligonucleotide primer can be naturally occurring, as in a purified restriction digest, or be produced synthetically. The primer is preferably single-stranded for maximum efficiency in amplification.

As used herein, "primer pair" refers to two primers, a forward primer and a reverse primer, that are capable of participating in PCR amplification of a segment of nucleic acid in the presence of a nucleic acid polymerase to produce a PCR amplicon. The primers that comprise a primer pair can be specific to the same HPV gene, resulting in an amplicon that consists of a sequence of nucleotides derived from a single HPV gene. Alternatively, the primers that comprise a primer pair can be specific to different HPV genes that reside within close proximity to each other within the HPV genome, thereby producing amplicons that consist of a sequence of nucleotides derived from more than one gene.

As used herein, "different imaging spectra," in reference to the fluorophores of the present invention, means that each fluorophore emits energy at a differing emission maxima relative to all other fluorophores used in the particular assay. The use of fluorophores with unique emission maxima allows the simultaneous detection of the fluorescent energy emitted by each of the plurality of fluorophores used in the particular assay.

As used herein, the term "discriminatory," used in reference to the oligonucleotide primers and probes of the present invention, means that said primers and probes are specific to a single HPV type. It includes HPV primers and probes specific to a single HPV type, but that share some homology with other HPV types. "Discriminatory" primers and probes of the present invention include those oligonucleotides that lack 3' homology with other HPV types in at least one nucleotide or more. Such a residue that is unique for the specific HPV type at the specific position and acts to discriminate the HPV type from the others in the alignment is referred to as a "discriminatory base". The term "discriminatory," in reference to oligonucleotides, does not include primers and probes that are specific to more than one HPV type, i.e. those that share full homology with greater than one HPV type. In this regard the degenerate primer/probe sets disclosed herein do not discriminate for the HPV type for which they are configured. For example, for the degenerate primer/probe set that targets HPV types 39 and 68, the primer/probe set for HPV type 39 has a preference for HPV type 39 over HPV type 68 but does not discriminate for HPV type 39 over HPV type 68. Because the degenerate primer/probe sets do not discriminate between the HPV types, the probes preferably have the same signal moiety. Since the assay is configured to determine the presence or absence of these HPV types in the aggregate, there is no need to use two optical channels for this purpose. Furthermore, when the degenerate primer/probe set is combined with other primer/probe sets in a single microwell for a multiplex assay, the signal moieties for the other primer/probe sets (either discriminatory or non-discriminatory) can be the same or different. The signal moieties for the assay are largely a matter of design choice. The skilled person will use the same signal moieties for primer/probe sets in the same microwell when it is necessary to know if the particular HPV type is present. The same signal moiety may be used on primer/probe sets for different HPV serotypes when it is sufficient to know if only one of those types is present.

As used herein, "amplicon" refers to a specific product of a PCR reaction, which is produced by PCR amplification of a sample comprising nucleic acid in the presence of a nucleic acid polymerase and a specific primer pair. An amplicon can consist of a nucleotide sequence derived from a single gene of a single HPV type or an amplicon can consist of a nucleotide sequence derived from more than one gene of a single HPV type.

As used herein, "primer/probe set" refers to a grouping of a pair of oligonucleotide primers and an oligonucleotide probe that hybridize to a specific nucleotide sequence of a single HPV type. Said oligonucleotide set consists of: (a) a forward discriminatory primer that hybridizes to a first location of a nucleic acid sequence of an HPV type; (b) a reverse discriminatory primer that hybridizes to a second location of the nucleic acid sequence of the HPV type downstream of the first location and (c) a fluorescent probe labeled with a fluorophore and a quencher, which hybridizes to a location of the nucleic acid sequence of the HPV type between the primers. In other words, an oligonucleotide set consists of a set of specific PCR primers capable of initiating synthesis of an amplicon specific to a single HPV type, and a fluorescent probe which hybridizes to the amplicon.

As used herein, "plurality" means two or more.

As used herein, "specifically hybridizes," in reference to oligonucleotide sets, oligonucleotide primers, or oligonucleotide probes, means that said oligonucleotide sets, primers or probes hybridize to a nucleic acid sequence of a single HPV type.

As used herein, "gene" means a segment of nucleic acid involved in producing a polypeptide chain. It includes both translated sequences (coding region) and 5' and 3' untranslated sequences (non-coding regions) as well as intervening sequences (introns) between individual coding segments (exons). For purposes of the description of the embodiments of the present invention, the HPV genome has a plurality of genes: e.g., L1, L2, and E1, E2, E4-E7.

As used herein, "locus" refers to the position on a chromosome at which the gene for a trait resides. The term locus includes any one of the alleles of a specific gene. It also includes homologous genes from different HPV types. For example, PCR assays that detect the L1 gene in HPV16 and HPV6 are single-locus assays, despite the detection of sequences from different HPV types. Contrarily, for example, assays that detect the L1 gene and the E1 gene of a single HPV type are multiple locus assays, even though a single HPV type is detected.

As used herein, "HPV" means human papillomavirus. "HPV" is a general term used to refer to any type of HPV, whether currently known or subsequently described.

As used herein, "fluorophore" refers to a fluorescent reporter molecule which, upon excitation with a laser, tungsten, mercury or xenon lamp, or a light emitting diode, releases energy in the form of light with a defined spectrum. Through the process of fluorescence resonance energy transfer (FRET), the light emitted from the fluorophore can excite a second molecule whose excitation spectrum overlaps the emission spectrum of the fluorophore. The transfer of emission energy of the fluorophore to another molecule quenches the emission of the fluorophore. The second molecule is known as a quencher molecule. The term "fluorophore" is used interchangeably herein with the term "fluorescent reporter".

As used herein "quencher" or "quencher molecule" refers to a molecule that, when linked to a fluorescent probe comprising a fluorophore, is capable of accepting the energy emitted by the fluorophore, thereby quenching the emission of the fluorophore. A quencher can be fluorescent, which releases the accepted energy as light, or non-fluorescent, which releases the accepted energy as heat, and can be attached at any location along the length of the probe.

As used herein "dark quencher" refers to a non-fluorescent quencher.

As used herein, "probe" refers to an oligonucleotide that is capable of forming a duplex structure with a sequence in a target nucleic acid, due to complementarity of at least one sequence of the probe with a sequence in the target region, or region to be detected. The term "probe" includes an oligonucleotide as described above, with or without a fluorophore and a quencher molecule attached. The term "fluorescent probe" refers to a probe comprising a fluorophore and a quencher molecule.

As used herein, "FAM" refers to the fluorophore 6-carboxy-fluorescein.

Other embodiments of the invention use different oligonucleotide sequences that bind to the E6/E7 gene region of HPV. The oligonucleotides described herein have a sequence that is capable of binding to the target nucleic acid sequence (and its complementary strand). The oligonucleotides described herein may also be used, either alone or in combination, to facilitate detection through amplification of the HPV E6/E7 gene nucleic acid sequence. In one embodiment, the probes are designed to perform a Taq-Man® real-time PCR assay on the target portion of the gene. Examples of three degenerate probes sets used for Taq-Man® real-time PCR assays, described in terms of their oligonucleotide sequences, are described below.

Specifically, in the first embodiment where the first degenerate primer/probe set is for HPV types 39 and 68, the primer/probe set that prefers HPV type 39 are SEQ ID NOS: 1, 3 and 5. The primer/probe set that prefers HPV type 68 are SEQ ID NOS: 2, 4 and 6. SEQ ID NOS: 1 and 2 are both Taq-Man forward primers and are degenerate with respect to each other. SEQ ID NOS 3 and 4 are both Taq-Man reverse primers and are degenerate with respect to each other. SEQ ID NOS 5 and 6 are both Taq-Man probes and are degenerate with respect to each other. The degenerate primer/probe sets for HPV types 33 and 58 are SEQ ID NOS. 7-16, which include two alternative reverse primer sequences, SEQ ID NOS. 13 and 14 being preferred. The degenerate primer/probe sets for HPV types 56 and 66 are SEQ ID NOS. 17-23.

The primer/probe sequences that select or discriminate for HPV serotype 51 are SEQ ID NOS. 24-29. The primer/probe sequences that select or discriminate for HPV Type 59 are SEQ ID NOS. 30-35. All the sequences referenced above are enumerated in Table 1 below. In the table below, "D" is detector, "FP" is forward primer, and "RP" is reverse primer.

TABLE 1

| SEQ ID NO: | Name | Description | Oligonucleotide Sequence: 5'-3' |
|---|---|---|---|
| SEQ ID NO: 1 | GR39_68E6 FP2 (39) | HPV 39 E6 Taq-Man Forward Primer | CCACTAGCTGCATGC CAATC |
| SEQ ID NO: 2 | GR39_68E6 FP2 (68) | HPV 68 E6 Taq-Man Forward Primer | CCATTAGCTGCATGC CAATC |
| SEQ ID NO: 3 | GR39_68E6 RP4 (39) | HPV 39 E6 Taq-Man Reverse Primer | CTAATGTAGTTGCAT ACACCGA |
| SEQ ID NO: 4 | GR39_68E6 RP4 (68) | HPV 68 E6 Taq-Man Reverse Primer | CTAATGTTGTTGCAT ACACCGA |
| SEQ ID NO: 5 | GR39_68D5 (39) | HPV 39 E6 Taq-Man Probe | GAGTAATATCGTAGC TCCCGTATTTT |
| SEQ ID NO: 6 | GR39_68D5 (68) | HPV 68 E6 Taq-Man Probe | GAGTAATATCGTAGT TCCCGTATTTT |
| SEQ ID NO: 7 | GR33_58FP2 (33) | HPV 33 E6 Taq-Man Forward Primer | TGTGCCAAGCATTGG AGACA |
| SEQ ID NO: 8 | GR33_58FP2 (58) | HPV 58 E6 Taq-Man Forward Primer | TGTGTCAGGCGTTGG AGACA |
| SEQ ID NO: 9 | GR33_58RP2 (33) | HPV 33 E6 Taq-Man Reverse Primer | CAAATGGATTTCCCT CTCTATA |
| SEQ ID NO: 10 | GR33_58RP2 (58) | HPV 58 E6 Taq-Man Reverse Primer | CAAATGGATTTCCAT CTCTATA |
| SEQ ID NO: 11 | GR33_58RP3 (33) | HPV 33 E6 Taq-Man Reverse Primer | CCTCTCTATATACAA CTGTTAAA |
| SEQ ID NO: 12 | GR33_58RP3 (58) | HPV 58 E6 Taq-Man Reverse Primer | CCATCTCTATACACT ATTCTTAAA |
| SEQ ID NO: 13 | GR33_58RP4 (33) | HPV 33 E6 Taq-Man Reverse Primer | AAATGGATTTCCCTC TCTATATAC |
| SEQ ID NO: 14 | GR33_58RP4 (58) | HPV 58 E6 Taq-Man Reverse Primer | AAATGGATTTCCATC TCTATACAC |

TABLE 1-continued

| SEQ ID NO: | Name | Description | Oligonucleotide Sequence: 5'-3' |
|---|---|---|---|
| SEQ ID NO: 15 | GR33_58D1 (33) | HPV 33 E6 Taq-Man Probe | TCATATACCTCAGAT CGTTGCAAAG |
| SEQ ID NO: 16 | GR33_58D1 (58) | HPV 58 E6 Taq-Man Probe | TCATATACCTCAGAT CGCTGCAAAG |
| SEQ ID NO: 17 | MP56_66FP (56) | HPV 56 E7 Taq-Man Forward Primer | ACCTAATACACGTAC CTTGTT |
| SEQ ID NO: 18 | MP56_66FP (66) | HPV 66 E7 Taq-Man Forward Primer | ACCTAATTCACGTAC CTTGTT |
| SEQ ID NO: 19 | MP56_66RP (56) | HPV 56 E7 Taq-Man Reverse Primer | ACACGCAGGTCCTCT TTGGT |
| SEQ ID NO: 20 | MP56_66RP (66) | HPV 66 E7 Taq-Man Reverse Primer | ACACGTAGCTCCTCT TTGGT |
| SEQ ID NO: 21 | MP56_66D (56) | HPV 56 E7 Taq-Man Probe | TGTAAGTTTGTGGTG CAGTTGGACA |
| SEQ ID NO: 22 | MP56_66D (66.1) | HPV 66 E7 Taq-Man Probe | TGTGAGCTTGTGGTG CAGTTGGACA |
| SEQ ID NO: 23 | MP56_66D (66.2) | HPV 66 E7 Taq-Man Probe | TGTGAGTTGGTGGTG CAGTTGGACA |
| SEQ ID NO: 24 | 51E6 FP | HPV 51 E6 Forward Primer | GCAGTATGCAAACAA TGTTCAC |
| SEQ ID NO: 25 | 51E6 RP | HPV 51 E6 Reverse Primer | TAGTAATTGCCTCTA ATGTAGTA |
| SEQ ID NO: 26 | 51E6 D | HPV 51 E6 Taq-Man Probe | CCTGCTATAACGTCT ATACTCTCTA |
| SEQ ID NO: 27 | 51E7 FP | HPV 51 E7 Forward Primer | CTCAGAGGAGGAGGA TGAAG |
| SEQ ID NO: 28 | 51E7 RP | HPV 51 E7 Reverse Primer | TGAACACCTGCAACA CGGAG |
| SEQ ID NO: 29 | 51E7 D | HPV 51 E7 Taq-Man Probe | CTACCAGAAAGACGG GCTGGAC |
| SEQ ID NO: 30 | 59E6 FP | HPV 59 E6 Forward Primer | GGAGAAACATTAGAG GCTGAA |
| SEQ ID NO: 31 | 59E6 RP | HPV 59 E6 Reverse Primer | ATAGAGGTTTTAGGC ATCTATAA |
| SEQ ID NO: 32 | 59E6 D | HPV 59 E6 Taq-Man Probe | ACCGTTACATGAGCT GCTGATACG |
| SEQ ID NO: 33 | 59E7 FP | HPV 59 E7 Forward Primer | GAAGTTGACCTTGTG TGCTAC |
| SEQ ID NO: 34 | 59E7 RP | HPV 59 E7 Reverse Primer | ATTAACTCCATCTGG TTCATCTT |
| SEQ ID NO: 35 | 59E7 D | HPV 59 E7 Taq-Man Probe | ATTACCTGACTCCGA CTCCGAGAA |
| SEQ ID NO: 36 | Target Region for Degenerate Primer Probe Sets for HPV Types 39 & 68 | 91 nucleotide Target Region | CCATTAGCTGCATGC CAATCATGTATTAAA TTTTATGCTAAAATA CGGGAACTACGATAT TACTCAGAATCGGTG TATGCAACAACATTA G |
| SEQ ID NO: 37 | Target Region for Degenerate Primer Probe Sets for HPV Types 33 & 58 | 138 nucleotide Target Region | TGTGCCAAGCATTGG AGACAACTATACACA ACATTGAACTACAGT GCGTGGAATGCAAAA AGACTTTGCAACGAT CTGAGGTATATGATT TTGCATTTGCAGATT TAACAGTTGTATATA GAGAGGGAAATCCAT TTG |
| SEQ ID NO: 38 | Target Region for Degenerate Primer Probe Sets for HPV Types 56 & 66 | 79 nucleotide Target Region | ACCTAATACACGTAC CTTGTTGTXAGTGTA AGTTTGTGGTGCAGT TGGACATTCAGAGTA CCAAAGAGGACCTGC GTGT |

The locations of the target regions for the primer/probe sets described in the above table are described in the following Table 1A:

TABLE 1A

Location of Target Regions

| Genotype | GenBank Accession # | Target Region Coordinates |
|---|---|---|
| 39 | M62849 | 287-377 |
| 68 | EU918769 | 181-271 |
| 33 | M12732 | 152-288 |
| 58 | D90400 | 153-289 |
| 56 | X74483 | 747-825 |
| 66 | EF177190 | 747-825 |

While there is sequence homology between the target regions for the degenerate primer/probe sets, the coordinates of these regions are genotype dependent.

In a further embodiment, the method includes treating a sample using at least one degenerate primer/probes set to select for two different but closely related HPV types and a primer/probe set that discriminates for a third HPV type, where the signal moiety for the degenerate probes emits a signal of the same wavelength and is, preferably, the same signaling moiety for the two degenerate probes. The signaling moiety of the primer/probe set that discriminates for the third HPV type emits signal at a wavelength that is different, and therefore separately detectable, from the wavelength emitted by the signaling moieties for the degenerate probes. These primer/probe sets are used in a nucleic acid amplification reaction for detecting the presence or absence of the amplified nucleic acid product.

In another embodiment, a kit is provided for the detection of HPV. The kit includes at least one degenerate primer/probes set that selects for two different but closely related HPV types and a primer/probe set that discriminates for a third HPV type, where the signal moiety for the degenerate probes emits a signal of the same wavelength and is, preferably, the same signaling moiety for the two degenerate probes. The signaling moiety of the primer/probe set that discriminates for the third HPV type emits signal at a wavelength that is different, and therefore separately detectable, from the wavelength emitted by the signaling moieties for the degenerate probes. The primer/probe sets capable of amplifying a target sequence that may be used for detection of that organism. The kit is provided with one or more of the oligonucleotides and buffer reagents for performing amplification assays.

In yet another aspect of the kit, oligonucleotides and reagents for purposes of Taq-Man PCR may be provided. In this aspect, three oligonucleotides are provided. Two of the three are amplification primers and the third oligonucleotide is configured as a detector.

BRIEF DESCRIPTION OF THE DRAWINGS

FIG. 1 illustrates the E6 gene target region for the HPV type 68 and schematically, the degeneracy of that target sequence among various mutations of HPV type 68, HPV type 39 and mutations of HPV type 39 along with the degenerate primer/probe set for HPV types 39 and 68;

FIG. 2A-B illustrates the E6 gene target region for the HPV type 33 and schematically, the degeneracy of that target sequence among various mutations of HPV type 33, HPV type 58 and mutations of HPV type 33 along with the degenerate primer/probe set for HPV types 33 and 58; and FIG. 3 illustrates the E7 gene target for HPV type 66 and schematically, the degeneracy of that target sequence among various mutations of HPV type 66, HPV type 56 and mutations of HPV type 56 along with the degenerate primer/probe set for HPV types 56 and 66.

DETAILED DESCRIPTION OF THE INVENTION

The oligonucleotide probes and probes sets described herein are specifically designed to select for or discriminate between HPV types. Specifically, degenerate primer/probe sets that are somewhat selective for one of two closely related HPV types are combined with at least one other primer/probe set that discriminates for yet a third HPV type that is different from the closely related HPV types.

The primer/probe sets provide a detectable signal when the specific HPV type is present in the sample.

In the preferred embodiments, the PCR (e.g. Taq-Man PCR), method of detection is used although other methods (e.g. TMA, and LCR) are also contemplated. Further, a kit for detecting more HPV types than there are channels for detection is disclosed.

Referring to FIG. 1, the degenerate primer/probe sets specific for HPV types are described in terms of their alignment with the illustrate target region of the E6 gene. FIG. 1 illustrates the forward primer region 10, the Taq-Man Detection Region 20 and the reverse primer region 30. FIG. 1 also illustrates the degenerate forward primers 11, 12, degenerate reverse primers 31, 32 and degenerate probes 21 and 22 in relation to their corresponding region on the target sequence 40. Only the variations in the target sequence 40 with respect to the forward primer region, reverse primer region and detector regions are illustrated in the boxes 60, 70 and 80. Sequence degeneracy between these regions are noted and from that it can be observed that these regions are less desirable because of increased sequence variation in these regions.

For example, in box 60 note that there are single nucleotide polymorphisms (T, C) between the portion of the target sequence 40 delimited by box 60 and the same E6 portion of an HPV type 39 target. Boxes 60, 70 and 80 illustrate the nucleotide polymorphisms relative to target for different strains of HPV types 68 and 39. These different strains, and the number and location of the nucleotide polymorphisms (relative to target) are reported in Table 2.

TABLE 2

| Polymorphisms Illustrated in FIG. 1 Relative to Target | |
|---|---|
| Type/Strain | Number of Polymorphisms (location from 5') |
| Type 68 | |
| 68_A7_High_45240-DQ80079. seq | 3 [T(@6); G(@66); T(@84)] |
| 68_A7_High_45240-EU918769.seq | None |
| BD115-68 900bp.seq | 3 [C(@21); A(@46); C(@81)] |
| BD-637-68 900 bp.seq | 1 [G(@31)] |
| T276-68 900bp.seq | None |
| T1177-68 900bp.seq | 3 [T or C (@6); C(@81); T or T(@84) |
| T1610-68 900bp 071309.seq | 2 [G(@53); C(@81)] |
| Type 39 | |
| 23, A7, High, 10568, M62849.seq | 6 [C(@4); A(@27); G (@51) G(@66); C(@69); T(@84)] |
| S492-39 900bp.seq | 8 [T(@3); C(@4); A(@27); G (@51) G(@66); C(@69); G(@80); T(@84)] |
| T296-39 900bp.seq | 7[C(@4); A(@27); G (@51); C(@57); G(@66); C(@69); T(@84)] |

The forward primer 11 for HPV 39 has a single nucleotide polymorphism and is therefore degenerate with respect to the forward primer 12 for HPV 68. Forward primer 11 is SEQ ID NO: 1 and forward primer 12 is SEQ ID NO: 2. The degeneracy between the two sequences is readily observed:

```
CCACTAGCTGCATGCCAATC

CCATTAGCTGCATGCCAATC
```

The respective degeneracy is indicated by underlining.

The degeneracy makes forward primer prefer to bind to HPV type 39 and forward primer 12 prefer to bind to HPV type 68. The degenerate primer/probes sets prefer to bind to the target of one HPV type to the other type but do not discriminate. In terms of the Figures, the primer/probe sets are described in relation to the target. Boxes 60, 70 and 80 contain information about degeneracy among HPV types 39 and 68 with respect to the target region 40 delimited by the boxes 60, 70 and 80. This is a location reference and not a hybridization reference. Specifically, the reverse primers 31 and 32 (SEQ ID NOs: 3 and 4) have sequences that are the reverse complement of the sequence in their corresponding location on target 40. Similarly, detector probes 21 and 22 (SEQ ID NOS: 5 and 6) are the reverse complement of the sequence in their corresponding location on target 40. Forward primers 11 and 12 (SEQ ID NOS: 1 and 2) are homologous to the sequence in their corresponding location on target 40.

FIG. 2A-B is similar to FIG. 1, but for degenerate primer/probe sets that select for HPV types 33 and 58. Boxes 160, 170 and 180 illustrate the nucleotide polymorphisms relative to target for different strains of HPV types 33 and 58. These different strains, and the number and location of the nucleotide polymporphisms (relative to target) are reported in Table 3. The location of the polymorphisms is illustrated in FIG. 2.

TABLE 3

Polymorphisms Illustrated in FIG. 2A-B Relative to Target

| Type/Strain | Number of Polymorphisms |
|---|---|
| Type 33 | |
| 33_A9_High_10586 EF422125.seq | 3 [C(@30); A(@62); C(@63)] |
| 33_A9_High_10586 EF422126.seq | 3 [C(@62); C(@63); T(@52)] |
| 33_A9_High_10586 EF566920.seq | 3 [C(@62); C(@63); A(@99)] |
| 33_A9_High_10586 EF566921.seq | 2 [C(@62); C(@63)] |
| 33_A9_High_10586 EF918766.seq | 4 [G(@58); C(@62); C(@63); G(@122)] |
| 33_A9_High_10586 GO374550.seq | 1 [A(@62)] |
| 33_A9_High_10586 GO374551.seq | 2 [G(@54); A(@62)] |
| 33_A9_High_10586 GO374552.seq | 2 [T(@10); A(@62)] |
| 33_A9_High_10586 M12732.seq | 2 [A(@62); C(@63)] |
| BD670 grp33 900bp.seq | 1 [A(@62)] |
| BD783-33 900bp.seq | 3 [C(@62); C(@63); C(@92)] |
| BD783-33 clone 900bp.seq | 2 [C(@62); C(@63)] |
| TI093-33 900bp.seq | 2 [G(@54); A(@62)] |
| Type 58 | |
| HPV_58 D60400.seq | 23 [See FIGS. 2A-B for location] |
| T-275-58 900bp.seq | 22 [See FIGS. 2A-B for location] |
| T-276-58 900bp.seq | 24 [See FIGS. 2A-B for location] |
| T-817-58 clone 900bp.seq | 23 [See FIGS. 2A-B for location] |
| 58_A9 High E6 10598 AF478160 | 23 [See FIGS. 2A-B for location] |
| 58_A9 High E6 10598 AF478167 | 22 [See FIGS. 2A-B for location] |
| 58_A9 High E6 10598 AF234531 | 23 [See FIGS. 2A-B for location] |
| 58_A9 High E6 10598 AF478157 | 23 [See FIGS. 2A-B for location] |
| 58_A9 High E6 10598 EU080239 | 25 [See FIGS. 2A-B for location] |
| 58_A9 High E6 10598 FJ407192 | 24 [See FIGS. 2A-B for location] |
| 58_A9 High E6 10598 G0248229 | 23 [See FIGS. 2A-B for location] |
| 58_A9 High E6 10598 G0248253 | 22 [See FIGS. 2A-B for location] |

FIG. 2A-B illustrates the forward primer region 110, the Taq-Man Detection Region 120 and the reverse primer region 130. FIG. 2A-B also illustrates the degenerate forward primers 111, 112, degenerate reverse primers 131, 132 and degenerate probes 121 and 122 in relation to their corresponding region on the target sequence 140. Only the variations in the target sequence 140 with respect to the forward primer region, reverse primer region and detector regions are illustrated in the boxes 160 (FIG. 2A), 170 and 180 (FIG. 2B).

For example, in box 160 note that there are single nucleotide polymorphisms (T, G, G) between the portion of the target sequence 140 delimited by box 60 and the same E6 portion of an HPV type 33 target. However, the forward primer 112 for HPV 58 has three single nucleotide polymorphisms and is therefore degenerate with respect to the forward primer 111 for HPV 33. Forward primer 111 is SEQ ID NO: 7 and forward primer 112 is SEQ ID NO: 8. The degeneracy between the two sequences is readily observed:

TGTGCCAAGCATTGGAGACA

TGTG<u>T</u>CAG<u>G</u>C<u>G</u>TTGGAGACA

The respective degeneracy is indicated by underlining.

The degeneracy makes forward primer 111 prefer to bind to HPV type 33 and forward primer 112 prefer to bind to HPV type 58. The degenerate primer/probes sets prefer to bind to the target of one HPV type to the other type but do not discriminate. In terms of the Figures, the primer/probe sets are described in relation to the target. Boxes 160, 170 and 180 contain information about degeneracy among HPV types 33 and 58 with respect to the target region 140 delimited by the boxes 160, 170 and 180. This is a location reference and not a hybridization reference. Specifically, the reverse primers 131 and 132 (e.g. SEQ ID NOS: 13 and 14) have sequences that are the reverse complement of the sequence in their corresponding location on target 140. Similarly, reverse probes 121 and 122 (SEQ ID NOS: 15 and 16) are the reverse complement of the sequence in their corresponding location on target 140. Forward primers 111 and 112 (SEQ ID NOS: 7 and 8) are homologous to the sequence in their corresponding location on target 140.

FIG. 3 is similar to FIGS. 1 and 2, but for degenerate primer/probe sets that select for HPV types 56 and 66. FIG. 3 illustrates the forward primer region 210, the Taq-Man Detection Region 220 and the reverse primer region 230. Boxes 260, 270 and 280 illustrate the nucleotide polymorphisms relative to target for different strains of HPV types 66 and 56. These different strains, and the number and location of the nucleotide polymporphisms (relative to target) are reported in Table 2.

TABLE 4

Polymorphisms Illustrated in FIG. 3 Relative to Target

| Type/Strain | Number of Polymorphisms (location from 5') |
|---|---|
| Type 66 | |
| 66_A6_High_37119-EF177191 | 6 [T(@8); A(@24); G(@30) C(@33); G(@71); A(@74)] |
| 66_A6_High_37119-EF177188 | 7 [T(@8); T(@9); A(@24); G(@30) C(@33); G(@71); A(@74)] |
| 66_A6_High_37119-EF177186 | 6 [T(@8); A(@24); G(@30) G(@35); G(@71); A(@74)] |
| Type 56 | |
| 56_A6_High 37119-EF177176 | 2 [G(@24); C(@56)] |
| 56_A6_High 37119-EF177178 | 3 [C(@20); C(@23); C(@24)] |
| 56_A6_High 37119-EF177179 | 1 [C(@24)] |
| 56_A6_High 37119-EF177180 | 1 [G(@24)] |
| BD616grp56 E7 | 3[G(@24); T(@54); C(@56)] |
| T1631-56 E7 | 1 [A(@24)] |

FIG. 3 also illustrates the degenerate forward primers 211, 212, degenerate reverse primers 231, 232 and degenerate probes 221 and 222 in relation to their corresponding region on the target sequence 240. Only the variations in the target sequence 240 with respect to the forward primer region, reverse primer region and detector regions are illustrated in the boxes 260, 270 and 280.

For example, in box 260 note that there are two single nucleotide polymorphisms (T, C) between the portion of the target sequence 240 delimited by box 260 between and HPV 66 target and an HPV 56 target. However, the forward primer2112 for HPV 56 has a single nucleotide polymorphism and is therefore degenerate with respect to the forward primer 211 for HPV 66. Forward primer 211 is SEQ ID NO: 17 and forward primer 212 is SEQ ID NO: 18. The degeneracy between the two sequences is readily observed:

ACCTAATACACGTACCTTGTT

ACCTAATTCACGTACCTTGTT

The respective degeneracy is indicated by underlining.

The degeneracy makes forward primer 211 prefer to bind to HPV type 56 and forward primer 212 prefer to bind to HPV type 66. The degenerate primer/probes sets prefer to bind to the target of one HPV type to the other type but do not discriminate. In terms of the Figures, the primer/probe sets are described in relation to the target. Boxes 260, 270 and 280 contain information about degeneracy among HPV types 56 and 66 with respect to the target region 240 delimited by the boxes 260, 270 and 280. This is a location reference and not a hybridization reference. Specifically, the reverse primers 231 and 232 (SEQ ID NOS: 19 and 20) have sequences that are the reverse complement of the sequence in their corresponding location on target 240. Similarly, probes 221 and 222 (SEQ ID NOS: 22 and 23) are the reverse complement of the sequence in their corresponding location on target 240. Forward primers 211 and 212 (SEQ ID NOS: 17 and 18) are homologous to the sequence in their corresponding location on target 140. While not specifically discussed, the degeneracy between the reverse primers and probes in the degenerate primer probe sets is readily observed.

In addition to the examples of degenerate primer/probe sets described herein, the skilled person, based upon the description herein and the accompanying figures, would be able to identify other target regions of closely related serotypes for which degenerate primer/probe sets could be designed. As is readily observed by the Figures, desirable target regions will have few polymorphisms between the individual serotypes. Those polymorphisms that are present can be addressed in the design of the degenerate primer/probe set consistent with the manner described herein.

As described below, primers and probes can bind to target sequences even though they are less than 100% complementary with those regions. The requisite degree of complementarity depends on a variety of factors including the stringency of the binding conditions. Depending upon the stringency conditions employed, the primers and probes may be modified to include different bases in their sequence and still be sufficiently complementary to bind to the target region of the nucleic acid. Sufficiently complementary, as used herein include complementarity of 70% or more. In preferred embodiments, the complementarity of the primers/probes to their target sequence is at least 80% over the length of the binding portion of the primers/probes. More preferably, the complementarity of the primers and probes to their target sequences is 90% or more.

Said another way, the present invention contemplates primers and probes that have at least 70% homology with the primers and probes specifically identified herein by SEQ ID. In preferred embodiments, primers/probes that have at least 80% homology with the primers and probes specifically identified by SEQ ID herein are contemplated. More preferably, primers and probes that have at least 90% homology with the primers and probes specifically identified by SEQ ID herein are contemplated.

While the oligonucleotides described herein must be sufficiently complementary to bind their respective portions of the HPV target for which they discriminate, it is recognized at some point the sequence of the oligonucleotide becomes less complementary to its target and may bind other nucleic acid sequences. Therefore, it is desirable that the oligonucleotide probes remain sufficiently complementary with its respective portion of the target gene, and not lose selectivity for its respective target binding site.

The target binding sequence within the oligonucleotide amplification primer may generally be located at its 3' end. The target binding sequence may be about 10-25 nucleotides in length and may have hybridization specificity to the amplification primer. Thus, it is understood that one skilled in the art may change the target binding sequence to effectively change hybridization specificity of the amplification primer and direct hybridization to an alternative sequence.

It is understood to one skilled in the art that the oligonucleotides as used in amplification assays may be modified to some extent without loss of utility or specificity towards a target sequence. For example, as is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain target-specificity require only routine experimentation and are within the ordinary skill in the art.

As a general guide in designing oligonucleotides useful as primers, $T_m$ decreases approximately 1° C.–1.5° C. with every 1% decrease in sequence homology. Temperature ranges may vary between about 60° C. and 70° C., but the primers may be designed to be optimal at 60° C.±4° C. and the probes may be designed to be optimal at 70° C.±4° C. A further consideration when designing amplification primers may be the guanine and cytosine content. Generally, the GC content for a primer may be about 60-70%, but may also be less and can be adjusted appropriately by one skilled in the art. Annealing complementary and partially complementary nucleic acid sequences may be obtained by modifying annealing conditions to increase or decrease stringency (i.e., adjusting annealing temperature or salt content of the buffer). Modifications such as those to the disclosed sequences and any necessary adjustments of annealing conditions to maintain gene specificity require only routine experimentation and are within the ordinary skill in the art.

Amplification reactions employing the primers described herein may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product not amplifiable in subsequent amplification reactions. UDG may be inactivated by uracil DNA glycosylase inhibitor (Ugi) prior to performing the subsequent amplification to prevent excision of dU in newly-formed amplification products.

PCR DNA polymerase contemplated for use in the present invention has 5'-3' exonuclease activity (e.g., Sequencing Grade Taq from Promega or Deep Vent$_R$™ (exo-) DNA from New England BioLabs) are used. The probe hybridizes to the target downstream from the PCR amplification primers. The probe is displaced as the downstream endonuclease synthesis proceeds from the primers between which the probe is disposed. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. Linearization of the secondary structure and separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semi quantitative or quantitative information about the initial amount of target present. When more initial copies of the target sequence are present, donor fluorescence more rapidly reaches a selected threshold value (i.e., shorter time to positivity). The decrease in acceptor fluorescence similarly exhibits a shorter time to positivity, detected as the time required for reaching a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

For commercial convenience, oligonucleotides useful for specific detection and identification of HPV nucleic acids may be packaged in the form of a kit. Typically, such a kit contains at least one oligonucleotide described herein. Reagents for performing a nucleic acid amplification reaction may also be included with the HPV-specific oligonucleotides. For example, buffers, other oligonucleotides, nucleotide triphosphates, enzymes, etc. may be included. The components of the kit may be packaged together in a common container. Optionally instructions may be included that illustrate one described embodiment for performing a specific embodiment of the inventive methods. Other optional components may also be included in the kit, e.g., an oligonucleotide tagged with a label suitable for use as an assay probe, and/or reagents or means for detecting the label.

Furthermore, the kit may include oligonucleotides and reagents in dried or liquid format. The components of the kit may be more stable and easily manipulated when in dried format. The dried components of the kit may be added or pre-treated to a solid phase such as microtiter plate, microarray, or other appropriate receptacle, where the sample and buffer need only be added. This format facilitates assaying multiple samples simultaneously and is useful in high-throughput methods. The BD ProbeTec™ and Viper™ XTR instruments may be used.

The following Examples illustrate specific embodiments of the invention described herein. As would be apparent to skilled artisans, various changes and modifications are possible, and are contemplated within the scope of the invention described.

A Taq-Man PCR System for Detecting HPV is further described below using the primer/probes sets in Table 1 as an Example. The Primer Sets of Primers/Probes described in Table 1 above were designed to perform Taq-Man PCR on for HPV types 39 and 68 and 51. Specifically, in the first embodiment where the first degenerate primer/probe set is for HPV types 39 and 68, the primer/probe set that prefers HPV type 39 are SEQ ID NOS: 1, 3 and 5. The primer/probe set that prefers HPV type 68 are SEQ ID NOS. 2, 4 and 6.

Taq-Man real-time PCR is a type of quantitative PCR. Taq-Man uses a fluorogenic probe which is a single stranded oligonucleotide of 20-26 nucleotides and is designed to bind only the DNA sequence between the two PCR primers. In Taq-Man, reporter dyes and quencher dyes are attached to the probe. The probe is annealed to the DNA by alternating the temperature to denature and re-anneal the DNA. The Taq polymerase adds nucleotides to the target DNA and this removes the Taq-Man probe from the template DNA. When the reporter dye is separated from the quencher dye, the reporter dye emits energy which is detectable. The energy is quantified by a computer, which provides a signal indicating that the target was detected. Only the specific PCR product can generate the fluorescent signal in Taq-Man PCR.

In the example herein, thermal cycling is contemplated. After an initial denature step at 95° C. for 15 minutes, the PCR mixture of primer/probe sets and sample for the detection of the presence or absence of target is subjected to the thermal cycle of 55° C. for 1 minute followed by 95° C. for 30 seconds for forty cycles.

To practice Taq-Man PCR, two PCR primers with a preferred product size of 50-150 base pairs and a probe with a fluorescent reporter or fluorophore (e.g. 6-carboxyfluorescein (FAM) and tetrachlorofluorescin (TET)) and a quencher such as tetramethylrhodamine (TAMRA) or a dark quencher such as previously described is covalently attached to its 5' and 3′ ends are used. Suitable fluorescent reporters and fluorophores are well known and not described in detail herein.

TABLE 5

Examples of Taq-Man PCR Probes Sets for Taq-Man Assay of HPV Types 39, 68 and 51

| SEQ ID NO: | Probe description | Oligonucleotide 5′ Sequence 3′ | ORF Location (bp) Genbank Accession in () |
|---|---|---|---|
| SEQ ID NO: 1 | HPV 39 E6 Taq-Man Forward Primer | CCACTAGCTGCATGC CAATC | 287-306 (M62849) |
| SEQ ID NO: 2 | HPV 68 E6 Taq-Man Forward Primer | CCATTAGCTGCATGC CAATC | 181-200 (EU918769) |
| SEQ ID NO: 3 | HPV 39 E6 Taq-Man Reverse Primer | CTAATGTAGTTGCAT ACACCGA | 356-377 (M62849) |
| SEQ ID NO: 4 | HPV 68 E6 Taq-Man Reverse Primer | CTAATGTTGTTGCAT ACACCGA | 250-271 (EU918769) |
| SEQ ID NO: 5 | HPV 39 E6 Taq-Man Probe | GAGTAATATCGTAGC TCCCGTATTTT | 326-351 (M62849) |
| SEQ ID NO: 6 | HPV 68 E6 Taq-Man Probe | GAGTAATATCGTAGT TCCCGTATTTT | 220-245 (EU918769) |
| SEQ ID NO: 24 | HPV 51 E6 Forward Primer | GCAGTATGCAAACAA TGTTCAC | 277-298 (M62877) |
| SEQ ID NO: 25 | HPV 51 E6 Reverse Primer | TAGTAATTGCCTCTA ATGTAGTA | 351-373 (M62877) |
| SEQ ID NO: 26 | HPV 51 E6 Taq-Man Probe | CCTGCTATAACGTCT ATACTCTCTA | 315-339 (M62877) |
| SEQ ID NO: 27 | HPV 51 E7 Forward Primer | CTCAGAGGAGGAGGA TGAAG | 652-671 (M62877) |
| SEQ ID NO: 28 | HPV 51 E7 Reverse Primer | TGAACACCTGCAACA CGGAG | 738-757 (M62877) |
| SEQ ID NO: 29 | HPV 51 E7 Taq-Man Probe | CTACCAGAAAGACGG GCTGGAC | 692-713 (M62877) |

The probes are designed to anneal to the ORF location in the HPV E6/E7 gene that is noted in the Table. In this regard, the ORF locations for the primer probe/set for HPV 59 for both the E6 and E7 genes are listed in the following table.

TABLE 6

ORF Locations on E6/E7 for Primer/Probe Set for HPV Type 59

| SEQ ID NO: | Probe description | Oligonucleotide 5′ Sequence 3′ | ORF Location (bp) Genbank Accession in () |
|---|---|---|---|
| SEQ ID NO: 30 | HPV 59 E6 Forward Primer | GGAGAAACATTAGAG GCTGAA | 313-333 (X77858) |
| SEQ ID NO: 31 | HPV 59 E6 Reverse Primer | ATAGAGGTTTTAGGC ATCTATAA | 369-391 (X77858) |
| SEQ ID NO: 32 | HPV 59 E6 Taq-Man Probe | ACCGTTACATGAGCT GCTGATACG | 342-365 (X77858) |
| SEQ ID NO: 33 | HPV 59 E7 Forward Primer | GAAGTTGACCTTGTG TGCTAC | 605-625 (X77858) |
| SEQ ID NO: 34 | HPV 59 E7 Reverse Primer | ATTAACTCCATCTGG TTCATCTT | 660-682 (X77858) |
| SEQ ID NO: 35 | HPV 59 E7 Taq-Man Probe | ATTAACTCCATCTGG TTCATCTT | 631-654 (X77858) |

In addition to the primers and probes, Taq-Man PCR requires reagents that are used for regular PCR (e.g. polymerase, free nucleotides) as well as a real-time PCR machine for analyzing the data. The reagents and equipment are well known to those skilled in the art and are not discussed in detail herein.

Although the invention herein has been described with reference to particular embodiments, it is to be understood that these embodiments are merely illustrative of the principles and applications of the invention described herein. It is therefore to be understood that numerous modifications may be made to the illustrative embodiments and that other arrangements may be devised without departing from the spirit and scope of the invention described herein as defined by the appended claims.

The invention claimed is:

1. A probe set for the detection of multiple serotypes of human papillomavirus (HPV) comprising at least three oligonucleotide primer/probe sets, each of which comprises at least one oligonucleotide probe that is detectably labeled and has a nucleotide sequence length of about 10 to about 50 and at least two oligonucleotide primers each of which has a nucleotide sequence length of about 10 to about 150 wherein each primer/probe set is at least preferential for a specific serotype of the HPV organism wherein the first and second of the primer/probe sets are degenerate with respect to each other and wherein the degenerate probes each have a signal moiety that emits signal that is detectable on the same channel and wherein the third primer/probe set is not degenerate with respect to the first and second primer/probe sets and discriminates for a third serotype that is not the serotypes to which the degenerate primer/probe sets preferentially anneal and wherein the third primer/probe set has a signal moiety that emits signal at a wavelength that is the same or different from the wavelength of the probes in the first and second primer/probe sets, wherein the target for the degenerate primer/probe set is selected from the group consisting of SEQ ID NOS: 36-38.

2. The probe set of claim 1, wherein the degenerate primer/probe set target is SEQ ID NO: 36 and wherein the third primer/probe set is configured to discriminate for HPV serotype 51 and is not degenerate with respect to the first or second primer/probe set, wherein the third primer/probe set is selected from at least one of the sequences selected from the group consisting of SEQ ID NOS: 24-29 and sequences that are at least 70% homologous to SEQ ID NOS: 24-29; the first primer/probe set selects for HPV serotype 39 and does not discriminate for HPV 39 serotype with respect to HPV serotype 68, wherein the first primer/probe set is selected from at least one of the sequences selected from the group consisting of SEQ ID NOS: 1, 3 and 5 and sequences that are at least 70% homologous to SEQ ID NOS: 1, 3 and 5; and the second primer/probe set selects for HPV serotype 68 and does not discriminate for HPV 68 serotype with respect to HPV serotype 39, wherein the second primer/probe set is selected from at least one of the sequences selected from the group consisting of SEQ ID NOS: 2, 4 and 6 and sequences that are at least 70% homologous to SEQ ID NOS: 2, 4 and 6.

3. The probe set of claim 1, wherein the degenerate primer/probe set target is SEQ ID NO: 37 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 70% homologous to SEQ ID NOS: 30-35; the first primer/probe set selects for HPV serotype 33 and does not discriminate for HPV 33 serotype with respect to HPV serotype 58, wherein the first primer/probe set is selected from at least one of the sequences selected from the group consisting of SEQ ID NOS: 7, 9, 11, 13, and 15 and sequences that are at least 70% homologous to SEQ ID NOS: 7, 9, 11, 13, and 15; and the second primer/probe set selects for HPV serotype 58 and does not discriminate for HPV 58 serotype with respect to HPV serotype 33, wherein the second primer/probe set is selected from at least one of the sequences selected from the group consisting of SEQ ID NOS: 8, 10, 12, 14, and 16 and sequences that are at least 70% homologous to SEQ ID NOS: 8, 10, 12, 14, and 16.

4. The probe set of claim 1, wherein the degenerate primer/probe set target is SEQ ID NO: 38 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 70% homologous to SEQ ID NOS: 30-35; the first primer/probe set selects for HPV serotype 56 and does not discriminate for HPV 66 serotype with respect to HPV serotype 56, wherein the first primer/probe set is selected from at least one of the sequences selected from the group consisting of SEQ ID NOS: 17, 19 and 21 and sequences that are at least 70% homologous to SEQ ID NOS: 17, 19 and 21; and the second primer/probe set selects for HPV serotype 66 and does not discriminate for HPV 66 serotype with respect to HPV serotype 56, wherein the second primer/probe set is selected from at least one of the sequences selected from the group consisting of SEQ ID NOS: 18, 20, 22, and 23 and sequences that are at least 70% homologous to SEQ ID NOS: 18, 20, 22, and 23.

5. The probe set of claim 1, wherein the degenerate primer/probe set target is SEQ ID NO: 36 and wherein the third primer/probe set is configured to discriminate for HPV serotype 51 and is not degenerate with respect to the first or second primer/probe set, wherein the primer/probe set is selected from at least one of the sequences selected from the group consisting of SEQ ID NOS: 24-29 and sequences that are at least 80% homologous to SEQ ID NOS: 24-29; the first primer/probe set selects for HPV serotype 39 and does not discriminate for HPV 39 serotype with respect to HPV serotype 68, wherein the first primer/probe set is selected from at least one of the sequences selected from the group consisting of SEQ ID NOS: 1, 3, and 5 and sequences that are at least 80% homologous to SEQ ID NOS: 1, 3, and 5; and the second primer/probe set selects for HPV serotype 68 and does not discriminate for HPV 68 serotype with respect to HPV serotype 39, wherein the second primer/probe set is selected from at least one of the sequences selected from the group consisting of SEQ ID NOS: 2, 4 and 6 and sequences that are at least 80% homologous to SEQ ID NOS: 2, 4, and 6.

6. The probe set of claim 1, wherein the degenerate primer/probe set target is SEQ ID NO: 37 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 80% homologous to SEQ ID NOS: 30-35; the first primer/probe set selects for HPV serotype 33 and does not discriminate for HPV 33 serotype with respect to HPV serotype 58, wherein the first primer/probe set is selected from at least one of the sequences selected from the group consisting of SEQ ID NOS: 7, 9, 11, 13, and 15 and sequences that are at least 80% homologous to SEQ ID NOS: 7, 9, 11, 13, and 15; and the second primer/probe set selects for HPV serotype 58 and does not discriminate for HPV 58 serotype with respect to HPV serotype 33, wherein the second primer/probe set is selected from at least one of the sequences selected from the group consisting of SEQ ID NOS: 8, 10, 12, 14, and 16 and sequences that are at least 80% homologous to SEQ ID NOS: 8, 10, 12, 14, and 16.

7. The probe set of claim 1, wherein the degenerate primer/probe set target is SEQ ID NO: 38 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 80% homologous to SEQ ID NOS: 30-35; the first primer/probe set selects for HPV serotype 56 and does not discriminate for HPV 66 serotype with respect to HPV serotype 56, wherein the first primer/probe set is selected from at least one of the sequences selected from the group consisting of SEQ ID NOS: 17, 19 and 21 and sequences that are at least 80% homologous to SEQ ID NOS: 17, 19 and 21; and the second primer/probe set selects for HPV serotype 66 and does not discriminate for HPV 66 serotype with respect to HPV serotype 56, wherein the second primer/probe set is selected from at least one of the sequences selected from the group consisting of SEQ ID NOS: 18, 20, 22, and 23 and sequences that are at least 80% homologous to SEQ ID NOS: 18, 20, 22, and 23.

8. The probe set of claim 1, wherein the degenerate primer/probe set target is SEQ ID NO: 36 and wherein the third primer/probe set is configured to discriminate for HPV serotype 51 and is not degenerate with respect to the first or second primer/probe set, wherein the primer/probe set is selected from at least one of the sequences selected from the group consisting of SEQ ID NOS: 24-29 and sequences that are at least 90% homologous to SEQ ID NOS: 24-29; the first primer/probe set selects for HPV serotype 39 and does not discriminate for HPV 39 serotype with respect to HPV serotype 68, wherein the first primer/probe set is selected from at least one of the sequences selected from the group consisting of SEQ ID NOS: 1, 3 and 5 and sequences that are at least 90% homologous to SEQ ID NOS: 1, 3 and 5; and the second primer/probe set selects for HPV serotype 68 and does not discriminate for HPV 68 serotype with respect to HPV serotype 39, wherein the second primer/probe set is selected from at least one of the sequences selected from the group consisting of SEQ ID NOS: 2, 4 and 6 and sequences that are at least 90% homologous to SEQ ID NOS: 2, 4 and 6.

9. The probe set of claim 1, wherein the degenerate primer/probe set target is SEQ ID NO: 37 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 90% homologous to SEQ ID NOS: 30-35; the first primer/probe set selects for HPV serotype 33 and does not discriminate for HPV 33 serotype with respect to HPV serotype 58, wherein the first primer/probe set is selected from at least one of the sequences selected from the group consisting of SEQ ID NOS: 7, 9, 11, 13, and 15 and sequences that are at least 90% homologous to SEQ ID NOS: 7, 9, 11, 13, and 15; and the second primer/probe set selects for HPV serotype 58 and does not discriminate for HPV 58 serotype with respect to HPV serotype 33, wherein the second primer/probe set is selected from at least one of the sequences selected from the group consisting of SEQ ID NOS: 8, 10, 12, 14, and 16 and sequences that are at least 90% homologous to SEQ ID NOS: 8, 10, 12, 14, and 16.

10. The probe set of claim 1, wherein the degenerate primer/probe set target is SEQ ID NO: 38 and wherein the third primer/probe set is configured to discriminate for HPV serotype 59 and is not degenerate with respect to the first or second primer/probe set, wherein the primer/probe set is selected from at least one of the sequences selected from the group consisting of SEQ ID NOS: 30-35 and sequences that are at least 90% homologous to SEQ ID NOS: 30-35; the first primer/probe set selects for HPV serotype 56 and does not discriminate for HPV 66 serotype with respect to HPV serotype 56, wherein the first primer/probe set is selected from at least one of the sequences selected from the group consisting of SEQ ID NOS: 17, 19 and 21 and sequences that are at least 90% homologous to SEQ ID NOS: 17, 19 and 21; and the second primer/probe set selects for HPV serotype 66 and does not discriminate for HPV 66 serotype with respect to HPV serotype 56, wherein the second primer/probe set is selected from at least one of the sequences selected from the group consisting of SEQ ID NOS: 18, 20, 22, and 23 and sequences that are at least 90% homologous to SEQ ID NOS: 18, 20, 22, and 23.

11. A kit for the detection of multiple serotypes of human papillomavirus (HPV), the kit comprising at least three oligonucleotide primer/probe sets, each of which comprises at least one oligonucleotide probe that is detectably labeled and has a nucleotide sequence length of about 10 to about 50 and at least two oligonucleotide primers each of which has a nucleotide sequence length of about 10 to about 150 wherein each primer/probe set is at least preferential for a specific serotype of the HPV organism wherein the first and second primer/probe sets are degenerate with respect to each other and wherein the degenerate probes each have a signal moiety that emits signal that is detectable on the same channel and wherein the third primer/probe set is not degenerate with respect to the other two primer/probe sets and discriminates for a third serotype that is not the serotypes to which the degenerate primer/probe sets preferentially anneal and wherein the third primer/probe set has a signal moiety that emits signal at a wavelength that is the same or different from the wavelength emitted by the signal moieties of the probes in the degenerate primer/probe set, wherein the target for the degenerate primer/probe set for the first and second degenerate primer/probe sets is selected from the group consisting of SEQ ID NOS: 36-38.

12. The kit of claim 11, wherein the degenerate primer/probe set target is SEQ ID NO: 36, the first degenerate primer/probe set comprises SEQ ID NOS: 1, 3 and 5, and the second degenerate primer/probe set comprises SEQ ID NOS: 2, 4, and 6.

13. The kit of claim 11, where the degenerate primer/probe set target is SEQ ID NO: 37 and the first degenerate primer/probe set comprises SEQ ID NO: 7, SEQ ID NO: 15 and one of SEQ ID NOS: 9, 11 and 13 and the second degenerate primer/probe set comprises SEQ ID NO: 8, SEQ ID NO: 15 and one of SEQ ID NOS: 10, 12 and 14.

14. The kit of claim 11, where the degenerate primer/probe set target is SEQ ID NO: 38 and the first degenerate primer/probe set comprises SEQ ID NOS: 17, 19, and 21 and the second degenerate primer/probe set comprises SEQ ID NO: 18, SEQ ID NO: 20 and one of SEQ ID NO: 22 and 23.

15. The kit of claim 11, wherein the third primer/probe set is selected from the group consisting of SEQ ID NOS: 24-26, SEQ ID NOS: 27-29, SEQ ID NOS: 30-32 and SEQ ID NOS: 33-35.

16. The kit of claim 15, wherein the third primer probe set discriminates for HPV serotype 51 and is selected from the group consisting of SEQ ID NOS: 24-26 and SEQ ID NOS: 27-29.

17. The kit of claim 15, wherein the third primer probe set discriminates for HPV serotype 59 and is selected from the group consisting of SEQ ID NOS: 30-32 and SEQ ID NOS: 33-35.

18. The kit of claim 15, wherein the signal moiety of the detector probe of the third primer/probe set emits a wavelength that is the same as the wavelength emitted by the detector probe of the first and second primer/probe sets.

19. The kit of claim 15, wherein the signal moiety of the detector probe of the third primer/probe set emits a wavelength that is different from the wavelength emitted by the detector probe of the first and second primer/probe sets.

* * * * *